United States Patent [19]

Hay et al.

[11] Patent Number: 5,233,046

[45] Date of Patent: Aug. 3, 1993

[54] DIARYLACETYLENES, ENAMINES AND ACETYLENIC POLYMERS AND THEIR PRODUCTION

[76] Inventors: Allan S. Hay, 5015 Glencairn Avenue, Montreal, Quebec H3W 2B3; Martino Paventi, 11786 28th Avenue, Montreal, Quebec H1E 9Z7, both of Canada

[21] Appl. No.: 787,055

[22] Filed: Nov. 4, 1991

[51] Int. Cl.$^5$ .................. C07D 235/08; C07D 249/18
[52] U.S. Cl. .................................. 548/257; 548/250; 548/255; 548/262.2; 548/266.2; 548/266.4; 548/266.6; 548/304.4; 548/305.1
[58] Field of Search ............ 548/250, 255, 257, 262.2, 548/266.2, 266.4, 266.6, 325, 327, 304.4, 305.1

[56] References Cited

U.S. PATENT DOCUMENTS 4,513,131  4/1985  Reinhardt et al. ................... 526/285
5,011,998  4/1991  Hay et al. .............................. 564/384

FOREIGN PATENT DOCUMENTS 76628  4/1983  European Pat. Off. .

OTHER PUBLICATIONS

Katritzky et al, Chemical Abstracts, vol. 117 (1992) 89888q.
Katritzky et al, Chemical Abstracts, vol. 107 (1987) 236609j.
Yamazaki et al, Chemical Abstracts, vol. 104 (1985) 88485n.
Nair, Chemical Abstracts, vol. 82 (1975) 156237m.
J. Macromol. Sci.-Rev. Macromol, Chem.C19(1), 1-34 (1980).
J.Polymer.Sci.: Polym.Chem.Ed.: vol. 28 (1990).
Tetrahedron 47, 2683 (1991).
Journal of Polymer Science: Part A: Polymer Chemistry, vol. 28, 2207-2221 (1990).

*Primary Examiner*—Richard L. Raymond
*Attorney, Agent, or Firm*—Bachman & LaPointe

[57] ABSTRACT

Diarylacetylenes and diarylenamines are synthesized from a Schiff's base and an N-arylmethylheterocycle; these compounds are useful as intermediates for a variety of polymers; in particular an efficient process is provided for producing diaryl acetylenes useful in the efficient production of acetylene group-containing polymers which can be cross-linked to produce high strength polymers free of structural defects such as conventionally arise as a result of liberation of volatiles during the cross-linking.

5 Claims, No Drawings

DIARYLACETYLENES, ENAMINES AND ACETYLENIC POLYMERS AND THEIR PRODUCTION

BACKGROUND OF THE INVENTION i) Field of the Invention

This invention relates to processes for producing diarylacetylenes and enamines which are valuable in the synthesis of homopolymers and copolymers, for example, poly(arylether)s, polyesters, polycarbonates and polyformals.

ii) Brief Description of Prior Art

Advanced composite materials are made from combinations of high performance fibers, such as glass, graphite, carbon, silicon carbide or ceramic fibers, arranged in close packed alignment in the polymer as a matrix. Such composite materials provide a combination of strength and modulus superior to that of structural metals and alloys on an equal weight basis. Such composites are, for example, employed in military and commercial aircraft, and space vehicles, as well as in sports and sailboats.

These composite materials are expensive, and so their use is confined to relatively high cost items. On the other hand, even though the raw materials for these advanced composites are expensive, over 70% of the costs associated with such composites result from the processing costs for their manufacture.

In particular, the currently used manufacturing processes produce volatiles during curing of the polymer matrix and such volatiles produce voids in the matrix which act as sites for structural failure. In order to minimize void formation during evolution of volatiles, the cure must be carried out over a long period, under reduced pressure and this manufacturing requirement is a major factor in the production cost.

Acetylenic groups have been proposed in polymers in order to provide reactive sites for cross-linking the polymers when heated. The potential advantage of such acetylenic groups is that no volatiles will be produced during curing or cross-linking.

The acetylenic groups have been introduced into polymer chains as terminal groups, pendant groups or internal groups.

Acetylene precursor polymers have been reviewed by Hergenrother (P. M. Hergenrother, J. Marcromol. Sci.-Rev. Macromol. Chem. C19(1), 1-34 (1980).

Most of the polymers with terminal acetylenic groups, that have been synthesized contain unsubstituted ethynyl groups on the ends of the polymer chains and they are generally end-capped low molecular weight oligomers which are synthesized in order to provide easier processability. Reinhardt et al (B. A. Reinhardt, F. E. Arnold and M. R. Unroe, U.S. Pat. No. 4,513,131 (1985)) have synthesized the simple bis(-phenylethynylphenyl)ethers as potentially thermally curable resins and studied their thermal curing properties.

Polymers containing pendant phenylethynyl groups have been synthesized and these polymers have been thermally cured. Examples are described in the aforementioned Hergenrother article and in U.S. Pat. No. 4,375,536 (1983) of Hergenrother.

Polymers containing internal acetylene groups have been less studied. T. Takeichi, H. Date and Y. Takayama, J. Pol. Sci. Chem. Ed. 28, 1989 (1990) describes the synthesis of polyimides containing internal acetylene groups. The authors indicate that the diphenylacetylene groups must be linked in the metal position to provide effective cross-linking.

Synthesis of Diarylacetylenes

Synthetic methods are reviewed in "Comprehensive Organic Chemistry" Pergamonn Press, 1979, Vol. 1 and in The Chemistry of the Carbon-Carbon Triple Bond, Ed. Saul Patai, John Wiley & Sons 1978, Part 2.

I. Dehydrohalogenation Reactions

The most common method of synthesis is by dehydrohalogenation reactions of iodo, bromo or chloro compounds with strong bases, usually KOH, NaOH, alkoxides such as sodium methoxide or potassium tertiary butoxide or sodamide, or with hydrides, e.g. sodium hydride or with organometallic compounds such as butyl lithium.

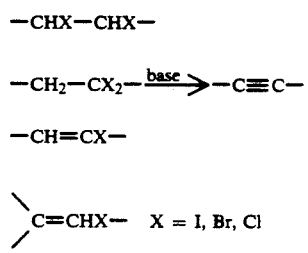

The elimination of other groups, thiols, sulfides, sulfonic acids, phosphate esters, trialkyl tin hydrides and the elimination of tertiary amines in a Hofmann elimination has also been observed (pp. 776-81 of the aforementioned S. Patai).

II. Displacement Reactions

Copper acetylides can react with aryl halides to give diarylacetylenes (p 796 of S. Patai) and aryl halides also react with acetylenes in the presence of palladium catalysts (p 798 of S. Patai):

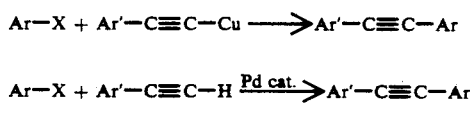

Benzotriazole, benzimidazole and triazoles, have been shown by Katritzky to behave as pseudohalogens in certain reactions, (e.g. A. R. Katritzky, Q.-H. Long and P. Lue, Tetrahedron Letters, 32,3597 (1991) they have demonstrated that dienamines can be synthesized from substituted benzotriazoles by reaction with sodium hydride.

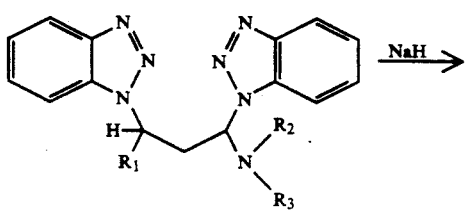

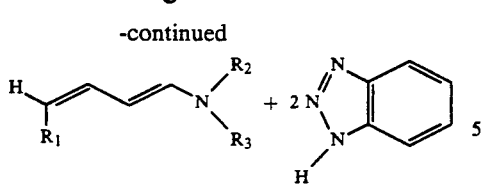

In this reaction the benzotriazole moiety behaves as a pseudohalogen and is eliminated with base in the same way a halogen like bromine would be. This is discussed further in a review article (A. R. Katritzky, S. Rachwal and G. J. Hutchings, Tetrahedron 47,2683 (1991).

The production of enamines is described in U.S. Pat. No. 5,011,998 (1991) of A. S. Hay et al. As described by Hay et al, the enamines are readily hydrolyzed to deoxybenzoins which in turn are readily oxidized to benzils which are useful in the production of a variety of polymers.

SUMMARY OF THE INVENTION

It is an object of this invention to provide a novel synthesis for chemical intermediates for polymer production.

It is a more particular object of this invention to provide processes for the production of diarylacetylenes.

It is a further particular object of this invention to provide a process for the production of enamines.

It is yet another particular object of this invention to provide novel enamines.

It is a still further object of this invention to provide a novel process for producing polymers having acetylenic linkages.

It is still a further object of this invention to provide novel polymers incorporating acetylenic linkages.

In accordance with one aspect of the invention there is provided a process for producing a chemical intermediate for polymer manufacture comprising: reacting a Schiff's base of formula (III):

$$Ar_1CH=NAr_2 \quad (III)$$

with an N-arylmethylheterocycle of formula (IV):

a basic medium wherein $Ar_1$, $Ar_2$ and $Ar_3$ are each independently selected from aryl and hetaryl, unsubstituted or substituted, one or more times, by radicals selected from F, Cl, Br; alkyl of 1 to 6 carbon atoms; alkenyl of 2 to 6 carbon atoms; aryl of to 12 carbon atoms; aralkyl of 7 to 18 carbon atoms; aralkenyl of 8 to 18 carbon atoms, alkoxy of 1 to 6 carbon atoms; thioalkoxy of 1 to 6 carbon atoms; aryloxy of 6 to 12 carbon atoms; and thioaryloxy of 6 to 12 carbon atoms; and —N    is a hetaryl radical.

If the process is operated under conditions favouring the elimination of the heterocyclic of formula (V):

the reaction proceeds to form a diarylacetylene of formula (I):

in which $Ar_1$ and $Ar_3$ are as defined above, as the favoured reaction.

If the process is operated under conditions which do not favour elimination of the heterocyclic of formula (V):

the reaction forms an enamine of formula (II):

wherein $Ar_1$, $Ar_3$ and —N    are all as defined above.

In another aspect of the invention there is provided enamines of formula (II), as defined above.

In yet another aspect of the invention there is provided a process for producing diarylacetylenes from the enamines (II).

In still another aspect of the invention there is provided a process of producing polymers and copolymers incorporating acetylenic compounds.

In yet another aspect of the invention there is provided novel polymers and copolymers having acetylenic groups incorporated therein.

DESCRIPTION OF PREFERRED EMBODIMENTS i) Synthesis of Intermediates

A novel synthesis of the invention comprises the reaction of the Schiff's base of formula (III), as defined above with the N-arylmethylheterocycle of formula (IV), as defined above in a basic medium.

This reaction can produce a diarylacetylene of formula (I), as defined above, or an enamine of formula (II), as defined above, or a mixture containing both.

The hetaryl radical —N    is, in particular, one which behaves as a pseudohalogen, and if the reaction conditions favour elimination of the heterocycle of formula (V):

the reaction proceeds with formation of the diarylacetylene (I) as the major reaction product, whereas if the reaction conditions do not favour elimination of heterocycle (V), the reaction proceeds with formation of the enamine (II) as the major reaction product.

In general, higher reaction temperatures in conjunction with strongly basic conditions favour the elimination reaction which results in the diarylacetylene (I) as the major reaction product. In contrast, lower reaction temperatures in conjunction with weakly basic conditions do not favour the elimination reaction, thus leading to the enamine (II) as the major reaction product.

Reaction time is also a factor in determining whether the diarylacetylene (I) or the enamine (II) is the dominant reaction product.

Depending on the inter-relationship between product may be predominantly the diarylacetylene (I) or the enamine (II), or a mixture of both in varying proportions.

The reaction resulting in the diarylacetylene (I) proceeds via the enamine (II) as an intermediate. The diarylacetylene (I) can be produced from the intermediate enamine (II) in situ, or the enamine (II) can be recovered or isolated from the reaction medium and subjected to conditions favouring formation of the diarylacetylene (I).

Thus the invention contemplates reaction of the Schiff's base (III) and the N-arylmethylheterocycle (IV) under basic conditions favouring elimination of the heterocycle (V) so that the reaction proceeds to the diarylacetylene (I) via the enamine (II). The invention also contemplates reaction of (III) and (IV) under first basic conditions which do not favour eliminaton of the heterocycle (V) to produce the enamine (II), and thereafter, possibly with prior isolation of the enamine (II), reacting the enamine (II) under second basic conditions effective for elimination of the heterocycle (V) to produce the diarylacetylene (I).

The invention also contemplates the elimination process in which the diarylacetylene (I) is produced from the enamine (II), as starting material.

ii) Process Parameters for Synthesis

The synthesis i) is carried out under basic conditions, more especially in a basic medium.

In particular, the medium suitably comprises a polar, aprotic organic solvent, for example, dimethylformamide, dimethylacetamide or N-methylpyrrolidone, which medium is rendered basic. The base character may be achieved by the presence of a base, for example, sodium or potassium tert-butoxide, sodium amide or sodium dimethyl amide; the sodium dimethyl amide may be generated in situ from sodium in N,N-dimethyl formamide. Mixtures of the bases may be employed.

As indicated above the base selected plays a role in determining whether the formation of the diarylacetylene (I) or the enamine (II) is favoured.

Since some heterocycles (V) have a strongly acidic character, the heterocycle (V) formed as a by-product of the formation of the diarylacetylene (I) from the enamine (II), may act as a buffer in the reaction medium, weakening the basic character and favouring termination of the reaction with formation of enamine (II).

The synthesis can be carried out conveniently at temperatures in the range of 0° to 100° C.; while still lower or higher temperatures outside this range can be employed; there is no advantage in employing temperatures outside this range.

In general lower temperatures in the range favour the first stage of the reaction to produce enamine (II) as the major reaction product. On the other hand, higher temperatures alone do not dictate continuation of the reaction through the enamine (II) to the diarylacetylene (I); and at the higher temperatures, the reaction time and the strength of the basic character of the reaction medium play a significant role in determining which reaction product, (I) or (II), dominates; and, as indicated above, when considering the basic character of the reaction medium, it is not only the strength of the base employed which is to be considered, because the acidity of by-product heterocycle (V) also affects the basic character.

On the other hand, a surprisingly fast reaction to form a high yield of diarylacetylene (I) has been observed employing a basic reaction medium of potassium t-butoxide in dimethylformamide even when benzotriazole, which is strongly acidic, was formed as the by-product heterocycle (V). At a temperature of 75° C. the reaction proceeded to form the diarylacetylene in high yield in a reaction time of less than 1 minute.

At lower temperatures, however, the benzotriazole released buffered the reaction to favour the enamine (II) as the reaction product.

The rapid reaction with benzotriazole as the heterocyclic (V) presumably results from the high electron withdrawing character of the benzotriazolyl radical.

iii) Reactants

The Schiff's bases (III) are readily produced in condensation reactions between aromatic aldehydes and aromatic amines, a reaction fully described in prior literature.

The N-arylmethylheterocycles (IV) are readily produced by the reaction between arylmethylhalides and aromatic heterocyclic compounds under conditions for elimination of hydrogen halide, a reaction fully described in prior literature.

The aryl radicals $Ar_1$, $Ar_2$ and $Ar_3$ are suitably aromatic radicals independently selected from:

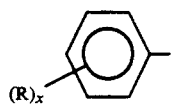

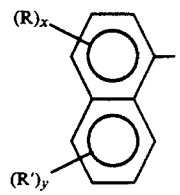

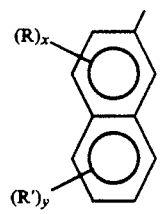

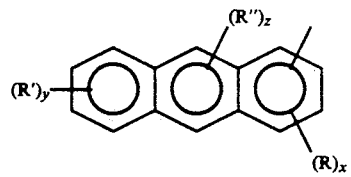

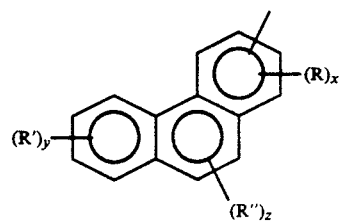

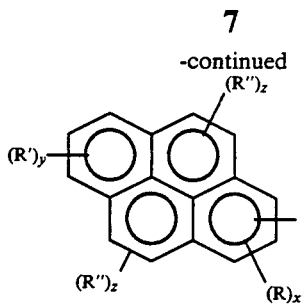

wherein x and y are integers independently selected from 0, 1, 2 or 3, z is an integer independently selected from 0, 1 or 2 and R, R' and R" are each independently selected from halogen atoms selected from fluorine, chlorine and bromine; alkyl of 1 to 6 carbon atoms, alkenyl of 2 to 6 carbon atoms; aryl of 6 to 12 carbon atoms, aralkyl of 7 to 18 carbon atoms; aralkenyl of 8 to 18 carbon atoms; alkoxy of 1 to 6 carbon atoms; thioalkoxy of 1 to 6 carbon atoms; aryloxy of 6 to 12 carbon atoms and thioaryloxy of 6 to 12 carbon atoms.

The hetaryl radicals $Ar_1$, $Ar_2$ and $Ar_3$ may be, for example, pyridinyl, furanyl, thiophenyl, thiazolyl or quinolinyl, which may be unsubstituted or substituted in the manner of the aryl radicals described above; for example the radicals:

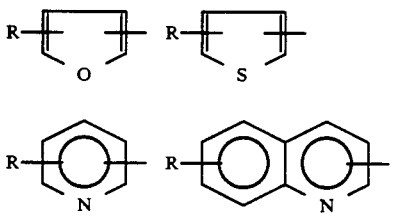

The heterocyclic radical:

—N may be, for example, a benzimidazolyl, benzotriazolyl, triazolyl or tetrazolyl, which radicals may be unsubstituted or substituted. It will be understood that the nature of the substituent is immaterial, provided that it does not interfere with the reaction to produce the desired enamine (II) or diarylacetylene (I).

iv) Polymer Production

Diarylacetylenes of formula (VI):

$$X_1-Ar_4-C\equiv C-Ar_5-X_2 \qquad (VI)$$

in which $X_1$ and $X_2$ are independently selected from F and OH, and $Ar_4$ and $Ar_5$ are aryl or hetaryl as defined for $Ar_1$ and $Ar_3$, are starting materials for producing polymers which incorporate acetylenic groups.

The diarylacetylenes (VI) in which $X_1$ and $X_2$ are both fluorine are within formula (I) and are produced by the previously described synthesis of the invention.

The diarylacetylenes (VI) in which at least one of $X_1$ and $X_2$ is a hydroxyl are produced from the corresponding diarylacetylenes (VI) in which $X_1$ and $X_2$ are fluorine, by hydrolysis of one or both fluorine substituents or etherification of one or both fluorine substituents and hydrolysis of the resulting alkoxy or aryloxy substituents.

The reaction to replace one or both fluorine substituents by an alkoxy or aryloxy is a novel reaction and it was surprising that such reaction would proceed efficiently. It appears that the acetylenic linkage activates the fluorine atom, facilitating its displacement, but this was not to have been expected. The reaction proceeds efficiently in the presence of an alkali metal alkoxide or aryloxide in a polar, aprotic organic solvent. The reaction is illustrated in the following scheme

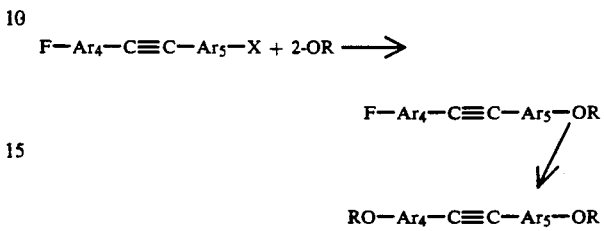

in which X is H or F and R is alkyl or aryl, and $Ar_4$ and $Ar_5$ are as defined previously.

The production of homopolymers and copolymers, particularly poly(arylether)s, polyesters, polycarbonates and polyformals from diarylacetylenes (VI) is illustrated below:

POLY(ARYL ETHER)S

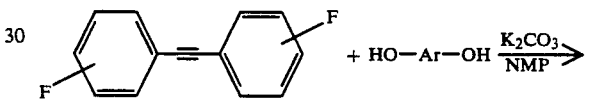

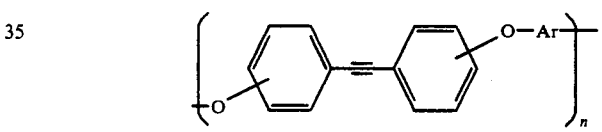

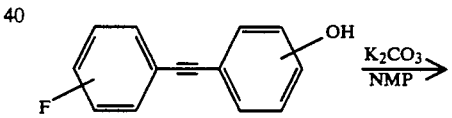

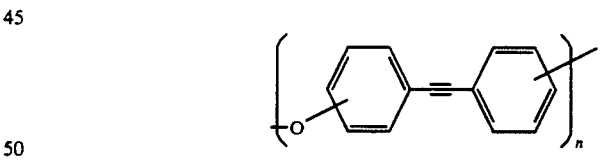

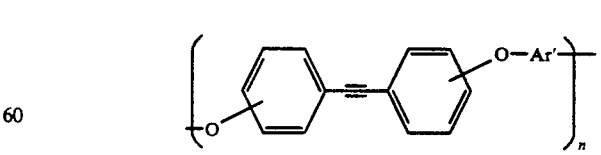

POLYESTERS

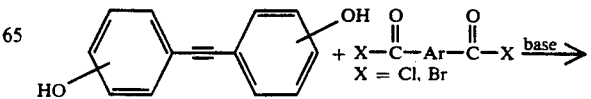

-continued

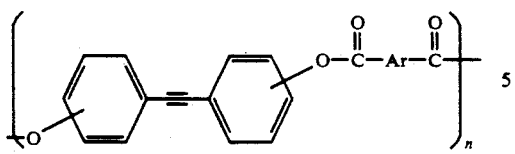

POLYCARBONATES and POLYFORMALS

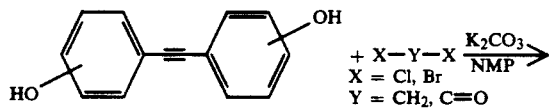

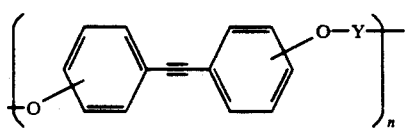

In these reactions n is an integer indicating the length of the polymer chain.

Any bisphenol can be employed as the reactant HO—Ar—OH— in the production of the poly(arylether). The radical $Ar_1$ is an aromatic moiety such as diphenylsulfone or benzophenone. When X is fluorine $Ar_1$ can also be a heterocyclic which activates the fluorine for nucleophilic substitution, for example, pyridine, benzoxazole, quinoxaline, an isoquinoline or a phthalazine.

Thus in another aspect of the invention there is provided a process for producing an acetylenic group-containing polymer or copolymer of the formula (VII):

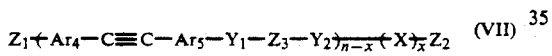  (VII)

wherein $Z_1$ is fluorine, hydroxyl or mercaptyl, $Z_2$ is hydrogen or fluorine, $Z_3$ is —O—, —S—, —CH$_2$—, —CO—, —CO—Ar$_6$—CO— or —Ar$_7$—, in which Ar$_6$ and Ar$_7$ are selected from divalent aromatic linkages, $Y_1$ and $Y_2$ are each selected from —O— and —S—, provided that when $Z_3$ is —O— or —S—, $Y_1$ and $Y_2$ are both single bonds, Ar$_4$ and Ar$_5$ are each independently selected from arylene and hetarylene, unsubstituted or substituted one or more times by radicals selected from F, Cl, Br, alkyl of 1 to 6 carbon atoms; alkenyl of 2 to 6 carbon atoms; aryl of 6 to 12 carbon atoms; aralkyl of 7 to 18 carbon atoms; aralkenyl of 8 to 18 carbon atoms, alkoxy of 1 to 6 carbon atoms, thioalkoxy of 1 to 6 carbon atoms, aryloxy of 6 to 12 carbon atoms and thioaryloxy of 6 to 12 carbon atoms; X is —Ar$_4$—C≡C—Ar$_5$ or a copolymer unit, n is an integer of 2 to 200, x is an integer of 0 to 199 and n is >x.

It will be understood that the two basic units of (VII) may be in a random or non-random arrangement or sequence in the case of a copolymer.

In still another aspect of the invention there is provided an acetylenic group-containing polymer or copolymer of formula (VII) as defined above provided that when the polymer or copolymer has acetylenic units —Ar$_4$—C≡C—Ar$_5$— at both terminal positions, n is at least 3.

The divalent linkages —Ar$_7$— are in particular derived from dihydroxy aromatics, for example, bisphenols, or from dihaloaromatics in which the halo groups are activated by the presence of electron withdrawing groups such as sulphonyl or carbonyl groups.

Aromatic groups having electron withdrawing groups are thus, for example:

and

in which the Ar groups are the same or different and are arylene or hetarylene.

The divalent aromatic linkages Ar$_6$ are selected from a broader class than Ar$_7$ since no electron withdrawing group is required in Ar$_7$.

The copolymer unit X may be derived from a wide variety of comonomers, for example, the following comonomer units in which the free valencies are in ortho or para positions.

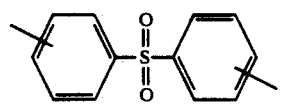

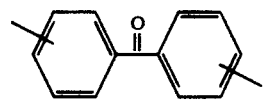

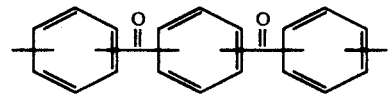

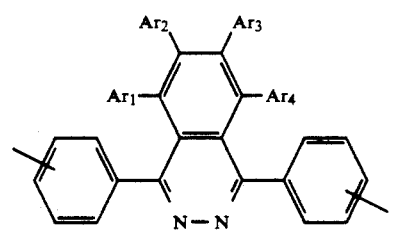

in which $Ar_1$, $Ar_2$, $Ar_3$ and $Ar_4$ are independently selected from unsubstituted and substituted aryl.

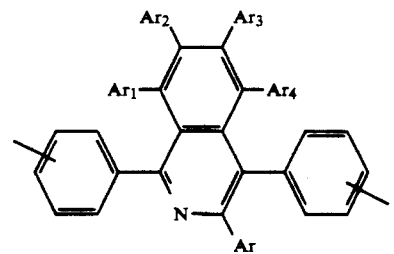

in which $Ar_1$, $Ar_2$, $Ar_3$ and $Ar_4$ are as defined above and Ar is aryl.

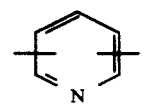

-continued

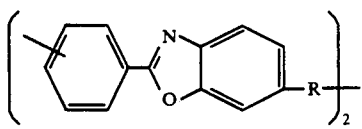

in which R₂ is alkylene or arylene

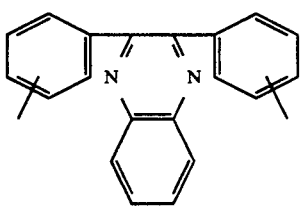

The aromatic moieties of the dihydroxy aromatics may be, for example, arylene and biarylene moieties including the following

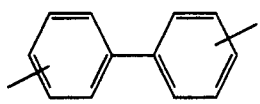

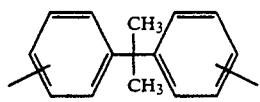

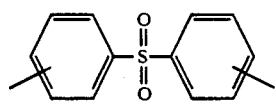

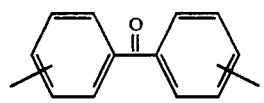

The diarylacetylenes (I) as a class can be readily oxidized to corresponding benzils useful in synthesis of a variety of polymers including polyquinoxalines, polyphenyls and phthalic anhydrides and the latter can be reacted with diamines to produce polyimides.

The enamines (II) of the invention are useful for the production of deoxybenzoins which can be oxidized to benzils which have utility in the production of polymers. The processes, involving use of enamines, described in U.S. Pat. No. 5,011,998, the teachings of which are hereby incorporated herein by reference, apply to the enamines (II) of the present invention.

Thus deoxybenzoins, benzils and polymers may be produced using the enamines (II) of this invention, and the procedures described in U.S. Pat. No. 5,011,998, incorporated herein by reference.

EXPERIMENTAL

I. Synthesis of N-Benzyl-substituted Heterocyclics

Ar = Aryl group

Ar₂H = 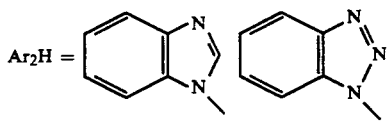

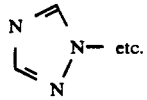 etc.

Example 1

(Phenylmethyl)-1H-benzimidazole

To benzyl chloride (13 g, 0.103 mol), 1h-benzimidazole (11.81 g, 0.10 mol), K₂CO₃ (60 g, 0.434 mol) was added acetonitrile (200 mL) and the mixture was stirred and heated under reflux for 3 h, filtered hot, and washed with hot CH₃CN (100 mL). The solvent of the filtrate was evaporated and the residual mass recrystallized as needles (16.5 g, 79%): mp 119°-120° C. (benzene)(lit[1] mp 105° C.); ¹H NMR (270 MHz, CDCl₃) δ 5.40 (s, 2H, CH₂), 7.20-7.41 (m, 8H), 7.85-7.89 (m, 1H), 8.02 (s, 1H, NCHN); IR (CDCl₃) 3093 (w), 3065 (w), 3037 (w), 2929 (w), 1615 (w), 1496 (s), 1456, 1385 (w), 1361, 1331, 1285, 1261, 1204, 1181, 1007 (w), 963 (w), 947 (w) cm⁻¹. MS (EI) m/e 208 (M⁺, 57.8), 91 (100); Anal. Calcd for C₁₄H₂₂N₂ (208.26): C, 80.74; H, 5.81; N, 13.45; Found: C, 80.70; H, 6.02; N, 13.31.

[1] Feigl, F.; Gleich, H. *Monatsh.* 1928, 49, 385-400.

Example 2

(Phenylmethyl)-1H-benzotriazole (Phenylmethyl)-1H-benzotriazole was prepared from 1H-benzotriazole (11.91 g, 0.100 mol) and benzyl chloride as in Example 1 for 1 hour to give the title compound and (phenylmethyl)-2H-benzotriazole in a ratio of 75:25. Workup and two recrystallizations gives the pure 1H-isomer: mp 117°-119° C. (CH₃CN); (lit.[1] mp 114°-117° C.; lit.[2,3] mp 115°-116° C.).

[1] Claramunt, R. M.; Elguero, J.; Garceran, R. *Heterocycles* 1985, 23, 2895.
[2] Märky, M; Schmid, H; Hansen, H. J. *Helv. Chim. Acta* 1979, 62, 2129.
[3] Rondeau, R. E.; Rosenberg, H. M.; Dunbar, D. J. *J. Mol Spectry.* 1969, 29, 305.

Example 3

(Phenylmethyl)-1H-[1,2,4-triazole]

(Phenylmethyl)-1H-[1,2,4-triazole] was prepared from 1H-[1,2,4-triazole] (69.7 g, 0.100 mol) and benzyl chloride as in Example 1 for 1 hour to give the title compound and (phenylmethyl)-2H-[1,2,4-triazole]. Workup and recrystallization gave the pure 1H-isomer (54%): mp 52°-53° C. (cyclohexane); (lit.[1] mp 54° C.).

[1] Claramunt, R. M.; Elguero, J.; Garceran, R. *Heterocycles* 1985, 28, 2895.

Example 4

(2-Naphthalenyl)methyl-1H-benzotriazole

A procedure similar to Example 2 from 1H-benzotriazole and 2-naphthylmethyl chloride gave the title compound after recrystallization in 45% yield: mp 152°–153° C. (CH$_3$CN); $^1$H NMR (200 MHz, CDCl$_3$) δ 6.03 (s, 2H, CH$_2$), 7.32–7.38 (m, 4H), 7.48–7.53 (m, 2H), 7.77–7.83 (m, 4H), 8.07–8.12 (m, 1H).

Example 5

(1-Naphthalenyl)methyl-1H-benzotriazole

A procedure similar to Example 2 from 1H-benzotriazole and 1-naphthylmethyl chloride gave the title compound after recrystallization in 85% yield: mp 149°–151° C. (EtOAc/petroleum ether 35°–60° C. abbreviated elsewhere as PE), $^1$H NMR (200 MHz, CDCl$_3$) δ 6.36 (s, 2H, CH$_2$), 7.29–7.59 (m, 7H), 7.87–7.93 (m, 2H), 8.06–8.11 (m, 1H), 8.21–8.26 (m, 1H).

Example 6

(4-Fluorophenyl)methyl-1H-benzotriazole

In a procedure as in Example 2 but using 1H-benzotriazole (23.8 g, 0.200 mol), 1-(chloromethyl)-4-fluorobenzene (29.0 g, 0.200 mol) and K$_2$CO$_3$ (70 g) in CH$_3$CN (300 mL) for 1 hour gave the title compound and (4-fluorophenyl)methyl-2H-benzotriazole. Workup and recrystallization gave the mixture of the 1H and 2H-isomers (75% yield) which was used in the subsequent reactions. A sample (5 g) was chromatographed (PE/EtOAc 9:1) eluting first the 2H isomer and then the title compound: mp 92°–94° C. (cyclohexane); $^1$H NMR (300 MHz, CDCl$_3$) δ 5.82 (s, 2H, CH$_2$), 7.00–7.06 (m, 2H), 7.25–7.46 (m, 5H), 8.08 (d, J=8.9 Hz, 1H); IR (CDCl$_3$) 3052 (w), 2938 (w), 1609, 1513, 1451 (w), 1351 (w), 1315 (w), 1269 (w), 1230 (s), 1159, 1084 cm$^{-1}$. MS (EI) m/e 227 (M$^+$, 52.6), 198 (100), 109 (96.9); Anal. Calcd or C$_{13}$H$_{10}$N$_3$F (227.24): C, 68.71; H, 4.44; F, 8.36; N, 18.49; Found: C, 68.44; H, 4.44; F, 8.40; N, 18.57.

Example 7

(3-Fluorophenyl)methyl-1H-benzotriazole

In a procedure as in Example 2 but using 1H-benzotriazole (20.6 g, 0.173 mol), 1-(chloromethyl)-3-fluorobenzene (25.0 g, 0.173 mol), K$_2$CO$_3$ (35.9 g) and CH$_3$CN (150 mL) for 1 h gave the title compound and (3-fluorophenyl)methyl-2H-benzotriazole. Similar workup and recrystallization gave the pure 1H-isomer (73%): mp 103°–104° C. (cyclohexane); $^1$H NMR (270 MHz, CDCl$_3$) δ 5.87 (s, 2H, CH$_2$), 6.97–7.08 (m, 3H), 7.29–7.49 (m, 4H), 8.10 (d, J=8.0 Hz, 1H); Anal. Calcd for C$_{13}$H$_{10}$N$_3$F (227.24): C, 68.71; H, 4.44; Found: C, 68.40; H, 4.67.

Example 8

(2-Fluorophenyl)methyl-1H-benzotriazole

In a procedure as in Example 2 but using 1H-benzotriazole (34.5 g, 0.289 mol) and 1-(chloromethyl)-2-fluorobenzene (41.8 g, 0.289 mol) for 1 h gave the title compound and (2-fluorophenyl)methyl-2-H-benzotriazole in a ratio of 80:20. Similar workup and recrystallization gave the pure 1H-isomer (73%): mp 93°–95° C. (cyclohexane); $^1$H NMR (270 MHz, CDCl$_3$) δ 5.93 (s, 2H, CH$_2$), 7.08–7.47 (m, 7H), 8.10 (d, J=7.2 Hz, 1H).

II. Synthesis of Schiff Bases

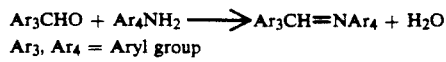

Ar$_3$, Ar$_4$ = Aryl group

Example 9

N-[(4-fluorophenyl)methylene]benzenamine

To 4-fluorobenzaldehyde (24.8 g, 0.200 mol) and aniline (18.6 g, 0.200 mol) was added benzene (200 mL) and acetic acid (0.7 mL) and the mixture is heated under reflux until all the water (3.6 mL) was azeotropically removed. The solvent is evaporated and the residual oil upon cooling and stirring crystallized. The white mass was then recrystallize as needles (28 g, 70%): mp 39°–40° C. (PE) (lit.[1] mp 40° C.).
[1]Dayal, S. K.; Ehrenson, S.; Taft, R. W. *J. Am. Chem. Soc.* 1972, 94, 9113.

Example 10

N-[3-fluorophenyl)methylene]benzenamine[1,2]

A similar procedure as for the preparation of N-[4-fluorophenyl)methylene]benzenamine (no acetic acid required) gave an oil which was distilled (87%): bp 100°–101° C./0.75 mm Hg.
[1]Liepins, E.; Pestunovich, V. A.; Tikhomirov, D. A.; Gaidarova, N. P. *Kim. Geterotsikl. Soedin.* 1977, 906–909; *Chem. Abstr.* 1977, 87, 183795b.
[2]Fauran, C. Bergeron, H.; Raynaud, G.; Thomas, J.; Eberle, J. Fr. Demande 2, 262, 513 Sep. 26, 1975; *Chem. Abstr.* 1976, 84, 121843 v.

Example 11

N-[(2-fluorophenyl)methylene]benzenamine

A similar procedure as for the preparation of N-[(4-fluorophenyl)methylene]benzenamine (no acetic acid required) gave an oil which was distilled (90%): bp 103°–104° C./1.5 mm Hg pressure; (lit.[1] bp 135° C.).
[1]Kessar, S. V.; Gopal, R.; Singh, M. *Tetrahedron* 1973, 29, 167.

III. Synthesis of Enamines

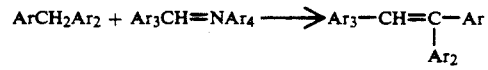

(1,2-diphenylethenyl)-1H-benzotriazole

Example 12

Method 1

To a mixture of powdered KOH (2.24 g, 0.040 mol) and DMF (18 mL) there was added with radpis stirring phenylmethyl-1H-enzotriazole (1.05 g, 0.005 mol) and N-phenylmethylenebezenamine (0.905 g, 0.005 mol) in DMF (7 mL) at 75° C. After five minutes the reactin was poured into ice-cold water (75 mL) and left to crystallize the title enamine. This was filtered, washed with water, and dried to yield 1.07 g (72%) of the titel enamine. An analytical sample was chromatographed PE/EtOAc 4:1 and recrystallized with charcoal treatement: mp 152°–154° C. (cyclohexane); Anal. Calcd for C$_{20}$H$_{15}$N$_3$ (297.36): C, 80.78; H, 5.08; N, 14.13; Found: C, 80.66; H, 5.14; N, 14.14.

Example 13

Method 2

A procedure similar to Example 12 except that instead of KOH potassium t-butoxide (0.56 g, 0.005 mol) was used. At 75° C. the reaction was complete and worked up as above. Chromatography first with PE elutes some (5–10%) diphenyl acetylene and then PE/EtOAc 4:1 elutes the title enamine (75–80%). This method was applied to other bases as given in Table 1.

Example 14

(1,2-Diphenylethenyl)-1H-benzimidazole

A procedure as in Example 13 using (phenylmethyl)-1H-benzimidazole gave the enamine (82%): mp 141°–143° C. (cyclohexane); $^1$H NMR (300 MHz, CDCl$_3$) δ 6.82 (m, 2H), 6.98 (d, J=8.0 Hz, 1H), 7.14–7.19 (m, 5H), 7.25–7.38 (m, 6H), 7.83 (s, 1H, NCH$\overline{N}$), 7 (88, J=d, 9.0 Hz, 1H); IR (CDCl$_3$) 3085 (w), 306$\overline{3}$, 3032 (w), 1635, 1611 (w), 1491 (s), 1484, 1452, 1391, 1365 (w), 1308, 1284, 1259, 1218, 1183 (w), 1078 (w), 1031 (w), 1006 (w) cm$^{-1}$. MS (EI) m/e 296 (M+, 100), 219 (13), 178 (52); Anal. Calcd for C$_{21}$H$_{16}$N$_2$ (296.38): C, 85.11; H, 5.44; N, 9.45; Found: C, 85.03; H, 5.50; N, 9.45.

Example 15

[1,2-bis(4-fluorophenyl)ethenyl)]-1H-benzotriazole

A procedure as in Example 13 using (4-Fluorophenyl)methyl-1H-benzotraizole. gave the title enamine (60%): mp 134°–136° C. (cyclohexane); MS (EI) m/e 333 (M+, 5), 305 (50), 304 (100), 303 (32), 215 (20), 214 (23), 183 (62); Anal. Calcd for C$_{20}$H$_{13}$F$_2$N$_3$ (333.34): C, 72.06; H, 3.93; F, 11.4; N, 12.61; Found: C, 72.28; H, 3.93; F, 11.11; N, 12.74 poured into ice-cold water (150 mL), extracted with CHCl$_3$ (3×50 mL) and chromatographed (PE). The acetylenes were recrystallized from MeOH. Thus was obtained: diphenylacetylene (75%): mp 59°–61° C. (MeOH); IR (CDCl$_3$) 1650 (w), 1604 (w), 1589 (w), 1512 (s), 1233, 1155 (w) cm$^{-1}$.

Example 17

Method b

To potassium t-butoxide (5.6 g, 50 mmol) in DMF (40 mL) at 75° C. was added N-(phenylmethyl)-1H-benzimidazole (2.08 g, 10 mmol) and N-(phenylmethylene)benzenamine (1.81 g, 10 mmol) dissolved in DMF (10 mL). After 5 hours the solution is poured into ice-cold water (150 mL), extracted with CHCl$_3$ (3×50 mL) and chromatographed (PE). Diphenylacetylene was obtained in 73% yield.

Example 18

Method c

To potassium t-butoxide (5.6 g, 50 mmol) in DMF (40 mL) at 75° C. was added N-(phenylmethyl)-1H-1,2,4-triazole (1.59 g, 10 mmol) and N-(phenylmethylene)benzenamine (1.81 g, 10 mmol) dissolved in DMF (10 mL). After 30 minutes the solution is poured into ice-cold water (150 mL), extracted with CHCl$_3$ (3×50 mL) and chromatographed (PE). Diphenylacetylene was obtained in 11% yield.

TABLE 1

Influence of different bases and temperatures on the reaction of phenylmethy-1H-benzotriazole (5 mmol) and N-phenylmethylenebenzenamine (5 mmol) in DMF (25 mL) in the production of the enamine (1) and diphenylacetylene (2).

| Example | Temp. (°C.) | Time (min) | Base (mmol) | | | | Yield (%) | |
|---|---|---|---|---|---|---|---|---|
| | | | NaNH2 | Na | t-BuOH | KOt-Bu | 1 | 2 |
| 19 | 75 | 30 | 0 | 22 | 0 | 0 | 0 | 55 |
| 20 | 75 | 50 | 0 | 4.8 | 2.3 | 0 | 55 | 5 |
| 21 | 60 | 30 | 0 | 9.1 | 4.6 | 0 | 61 | 0 |
| 22 | 75 | 60 | 0 | 4.8 | 0 | 0 | 32 | 0 |
| 23 | 50 | 20 | 0 | 0 | 0 | 5 | 40 | 35 |
| 24 | 22 | 20 | 0 | 0 | 0 | 2.5 | 60 | 0 |
| 25 | 0 | 80 | 0 | 0 | 0 | 3.57 | 56 | 0 |
| 26 | 75 | 70 | 15 | 0 | 0 | 0 | 47 | 5 |
| 27 | 75 | 1100 | 0 | 22 | 11 | 0 | 3 | 42 |

IV. Synthesis of Acetylates

ArCH$_2$Ar$_2$ + Ar$_3$CH=NAr$_4$ ⟶

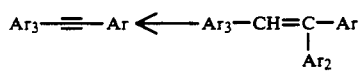

Ar$_3$—≡—Ar ⟵ Ar$_3$—CH=C—Ar
                                |
                               Ar$_2$

Ar, Ar$_3$, Ar$_4$ = Aryl groups

Diphenylacetylene
General Procedure

Example 16

Method a

To potassium t-butoxide (3.36 g, 30 mmol) in DMF (40 mL) at 75° C. was added as quickly as possible and all at once the [arylmethyl]-1H-benzotriazole (10 mmol) and N-(arylmethylene)benzenamine (10 mmol) dissolved in DMF (10 mL). Within a minute the solution is

Example 28

1-(Phenylethynyl)naphthalene

In a procedure similar to that of Example 16 using [phenylmethyl]-1H-benzotriazole (10 mmol) and N-([1-naphthalenyl]methylene)benzenamine (10 mmol): 88% yield: mp 51°–53° C. (MeOH) (lit$^1$ oil); $^1$H NMR (300 MHz, CDCl$_3$) δ 7.39–7.69 (m, 8H), 7.77–7.90 (m, 3H), 8.46 (br d, 2.7H, 1H); IR (CDCl$_3$) 3060 (s), 2245 (eyne), 1596, 1581, 1508, 1491 (s), 1442, 1398, 1333, 1215, 1070, 1017 cm$^{-1}$. MS (EI) m/e 228 (M+, 100).
$^1$Dessy, R. E.; Kandil, S. A. *J. Org. Chem.* 1965, 30, 3857.

Example 29

1-Methoxy-4-(phenylethynyl)benzene

Procedure similar to that of Example 16 using [phenylmethyl]-1Hbenzotriazole (10 mmol) and N-[(4-methoxyphenyl)methylene]benzenamine (10 mmol): 67% yield: mp 57°–58° C. (MeOH) (lit.$^1$ 58°–60° C.); $^1$H NMR (300 MHz, CDCl$_3$) δ 3.84 (s, 3H, OCH$_3$), 6.89 (d, 1.9H, 2H, C(3 and 5)H), 7.30–7.38 (m, 3H(), 7.45–7.54 (m, 4H).

[1]Katritzky, A. R.; Boulton, A. J.; Short, D. J. *J. Chem. Soc.* 1960, 1519.

Example 30

Bis(4-fluorophenyl)acetylene

To potassium t-butoxide (1.5 g, 13.4 mmol) in DMF (15 mL) at 75° C. was added as quickly as possible and all at once [(4-fluorophenyl)methyl]-1-H-benzotriazole (1.14 g, 5 mmol) and (4-fluorophenyl)methylenebenzenamine (1.00 g, 5 mmol) dissolved in DMF (10 mL). Within a minute the solution is poured into ice-cold water (75 mL) crystallizing the title compound which was filtered and then chromatographed (PE). The acetylene 0.54 g (50%) recrystallizes as needles: mp 95°-96° C. (MeOH); (lit.[1] 94°-95° C.).
[1]Gascoyne, J. M.; Mitchell, P. J.; Phillips, L. *J. Chem. Soc. Perkin Trans.* 2 1977, 1051.

Example 31

4-(t-Butoxy)-4'-fluorodiphenylacetylene

A similar procedure as for the preparation of bis(4-fluorophenyl)acetylene in Example 30 but stirred at 75° C. for 15 min and then quenched with water gave the title acetylene (15% HPLC) and bis(4-fluorophenyl)acetylene (30% HPLC). Chromatography (PE) elutes the difluoro derivative then PE/EtOAc 97:3 elutes the title compound recrystallizing as colorless plates 2.5 g (10%): mp 102°-104° C. (MeOH); $^1$H NMR (200 MHz, CDCl$_3$) δ 1.35 (s, 9H, (CH$_3$)$_3$), 6.93-7.06 (dd, J=8.6 Hz, 4H), 7.39-7.51 (m, 4H); IR (CDCl$_3$) 3020 (w), 2981, 2247 (w,(acetylenic stretch), 1605, 1515 (s), 1474 (w), 1393 (w), 1367, 1281 (w), 1234, 1218, 1157 (s) cm$^{-1}$. MS (EI) m/e 268 (M+ (4.5)), 212 (100), 183 (28), 157 (9.4); Anal. Calcd for C$_{18}$H$_{17}$FO (268.33): C, 80.57; H, 6.39; Found: C, 80.10; H, 6.42.

Example 32

4,4'Bis(t-Butoxy)diphenylacetylene

A similar procedure as for the preparation of bis(4-fluorophenyl)acetylene.] in Example 30 but using 5 equiv of potassium t-butoxide for 150 minutes and then quenched with water gave the title acetylene (45% HPLC). Chromatography (PE/EtOAc 9:1) and recrystallization with charcoal treatment gave 0.64 g (40%) colorless prisms: mp 129°-131° C. (MeOH); $^1$H NMR (300 MHz, CDCl$_3$) δ 1.36 (s, 18H, C(CH$_3$), 6.96 (d, J=8.7 Hz, 4H, phenyl C3and 3'H), 7.43 (d, 4H, phenyl C2 and 2'H); IR (CDCl$_3$) 3040 (w), 2980, 2936 (w), 2907, 2875, 1606, 1511, 1475 (w), 1394, 1367, 1309 (w), 1240, 1158 (s), 1101 (w), 1016 (w) cm$^{-1}$. MS (EI) m/e 322 (M+, 6.1), 266 ((4.1), 2.10 (100).

Example 33

1,2-Bis(4hydroxyphenyl)-ethanone

To a solution of acetic acid (15 mL), c. HCl (2.0 mL) and H$_2$O (3.0 mL) was added 1,1'-(1,2-ethynediyl)bis[4-(1,1-dimethylethoxy)benzene] (1.0 g, 3.1 mmol) and heated under reflux 1.5 h. Then the solution was poured into ice-cold H$_2$O (50 mL) precipitating the title compound which was filtered washed with water, air-dried, and recrystallized into tanned needles (0.52 g, 80% yield). A second recrystallization with charcoal treatment and acidification of the solution gave colorless needles: m 217°-220° C. (H$_2$O) (lit[1] mp 214°-215° C.); $^1$H NMR (300 MHz, DMSO-d$_6$) δ 4.09 (s, 2H, CH$_2$), 6.66 (d, J=8.45 Hz, 2H, C9H), 6.82 (d, J=8.7 Hz, 2H, C2H), 7.02 (d, 2H, C8H), 7.89 (d, 2H, C3H), 9.23 (s, 1H, C10OH), 10.34 (s, 1H, C1OH); $^{13}$C NMR (300 MHz, DMSO-d$_6$) δ 43.44 (CH$_2$), 115.11, 115.20, 125.58, 127.85, 130.36, 130.54, 131.02, 131.17, 155.85, 161.97 196.18 (C=O); MS (EI) m/e 228 (M+, 4), 121 (100), 107 (14.8), 93 (13), 65 (15).
[1]Zincke, Th.; Fries, K. *Justus Liebigs Ann. Chem.* 1902, 325, 67.

Example 34

1-Hydroxy-4-(phenylethynyl)benzene

A procedure similar to that described[1] was used. A sample of 1-methoxy-4-(phenylethynyl)-benzene (0.4 g, 1.9 mmol) was added collidine (3 mL), LiI (1.5 g) and the solution heated under reflux for 5 h (>95% conversion). The solution was poured into water acidified with HCl, extracted with ether (3×50 mL) and dried (MgSO$_4$). The ether was evaporated and the residue chromatographed (PE) eluting the title compound 0.3 g (80%): mp 125°-128° C. (cyclohexane) (lit[2] mp 91°-92°C., lit[3] mp 83°-84° C.); $^1$H NMR (300 MHz, DMSO-d$_6$) δ 6.80 (d, J=8.77 Hz, 2H, C2H), 7.37 (d, 2H, C3H), 7.35-7.42 (m, 3H), 7.46-7.50 (m, 2H), 9.92 (s, 1H, OH); $^{13}$C NMR (300 MHz, DMSO-d$_6$) δ 87.32 (acetylenic C), 89.98 (acetylenic C), 112.42 (sp$^2$C), 115.74, 122.90 (sp$^2$C), 128.20, 128.66, 131.06, 133.00, 158.06 (COH); IR (CDCl$_3$) 3596 (OH), 3066 (w), 3039 (w), 2217 (w, acetylenic stretch), 1605, 1512, 1429 (w), 1328 (w), 1261 (s), 1219, 1171 (s), 1140 (w), 1099 (w), 834, 805 (w) cm$^{-1}$. MS (EI) m/e 194 (M+, 100), 165 (29.4), 97 (11.3).
[1]Harrison, I. T. *J. Chem. Soc., Chem. Commun.* 1969, 616.
[2]Veschambre, H.; Dauphin, G.; Kergomard, A. *Bull. Soc. Chim. Fr.* 1967, 2846.
[3]Huysmans, W. G. W. *Dissertation Leiden* 1964.

Example 35

4,4'-Bis(phenoxy)diphenylacetylene

To 4,4'-difluorotolane (0.5 g, 0.0023 mol) and dry potassium phenolate (prepared from aqueous KOH and phenol with azeotropic removal of H$_2$O with benzene) (1.5 g, 0.011 mol) was added DMF (10 mL) and the mixture heated at 170° C. for 12 h after which there appeared a little difluorotolane remaining. This mixture was poured in water, the precipitate was filtered, washed with water, dried, and the title compound recrystallized as flakes 0.54 g (64%): mp 171°-173° C. (acetic acid) (lit.[1] mp 167°-168° C.); $^1$H NMR (270 MHz, CDCl$_3$) δ 6.89 (d, J=8.7 Hz, 4H, phenylene (C3,3'H), 6.97 (d, J=8.6 Hz, 4H, phenyl C2,2'H) 7.07 t, J=7.9 Hz, 2H, phenyl C4H), 7.29 (t, 4H, phenyl C3,3'H), 7.40 (d, 4H, phenylene C2,2'H); IR (CDCl$_3$) 3041 (w), 3020 (w), 1590, 1512, 1488, 1312 (w), 1274 (w), 1238 (s), 1218, 1165 (w), 1020 (w) cm$^{-1}$. When the sample is placed in a DSC apparatus with a N$_2$ gas flow ramped at 10° C./min it shows a Tm=163.9° C. In a gas-tight crucible and the temperature ramped at 2° C./min this sample shows Tm=169.5° C. and an exotherm maximum at 359.3° C. The exotherm begins at ~302° C. and ends at ~396° C. Some of this material is heated in a closed glass capillary tube at 320°-330° C. for 6 h and then an aliquot of the product was chromatographed (HPLC). The retention times (tR in min) and area % were: 4.43 (8), 4.63 (6), 9.02 (40), 13.08 (6.5), 19.24 (15).
[1]Lau, K. S.; Arnold, F. E. *Org. Prep. Proced. Int.* 1980, 12, 327.

Example 36

3,3'-Difluorodiphenylacetylene

A simile procedure to Example 30 but using [(3-fluorophenyl)methyl]-1H-benzotriazole and (3-fluorophenyl)methylenebenzenamine, gave the title acetylene after recrystallization (30%) needles: mp 60°-62° C. (MeOH) (lit.[1] mp 61°-62° C., lit.[2] mp 55.5°-58° C.); $^1$H NMR (300 MHz, CDCl$_3$) δ 7.04-7.11 (m, 2H), 7.22-7.25 (m, 2H), 7.31-7.35 (m, 4H); $^{13}$C NMR (300 MHz, CDCl$_3$) δ 88.89 (2.9, ethynyl C), 115.92 (21.1, C4), 118.42 (22.9, C2), 124.60 (9.5, C1), 127.54 (2.9, C6), 129.97 (8.7, C5), 162.36 (246.7, C3).

[1]Carpino, L. A.; Chen, H.-W., *J. Am. Chem. Soc.* 1979, 101, 390.
[2]Bender, D. F.; Thippesway, T.; Rellahan, W. L. *J. Org. Chem.* 1970, 35, 939.

Example 37

2,2'-Difluorodiphenylacetylene

A similar procedure to Example 30 but using [(2-fluorophenyl)methyl]-1H-benzotriazole and (2-fluorophenyl)methylenebenzenamine, gave the title acetylene after chromatography (PE) and recrystallization (15%) needles: mp 53°-54° C. (MeOH); $^1$H NMR (200 MHz, CDCl$_3$) δ 7.05-7.16 (m, 4H), 7.27-7.38 (m, 2H), 7.50-7.58 (m, 2H); $^{13}$C NMR (200 MHz, CDCl$_3$) δ 88.05 (2.6, acetylenic C), 112.03 (15.8, C1), 116.02 (21, C3), 124.49 (3.8, C6), 130.83 (8, C4), 134.06 (C5), 163.24 (253, C2); IR (CDCl$_3$) 3040 (w), 2228 (w, acetylenic stretch), 1951 (w), 1917 (w), 1883 (w), 1799 (w), 1700 (w), 1615 (w), 1576, 1501, 1447 (s), 1413 (w), 1321 (w), 1264 (s), 1224 (s), 115 (w), 1100, 1030 cm$^{-1}$. MS (EI) m/e 214 (M+, 100), 107 (12.8).

Example 38

2,4'-Difluorodiphenylacetylene

A similar procedure to Example 30 but using [(4-fluorophenyl)methyl]-1H-benzotriazole (1.14 g, 5 mmol) and (2-fluorophenyl)methylenebenzenamine (1.00 g, 5 mmol), gave the title acetylene after recrystallization (50%) needles: mp 108°-109° C. (MeOH); $^1$H NMR (200 MHz, CDCl$_3$) δ 7.0-7.18 (m, 4H), 7.24-7.38 (m, 1H), 7.45-7.59 (m, 3H); $^{13}$C NMR (200 MHz, CDCl$_3$) δ 82.77 (acetylenic C1), 93.72 (3.35, acetylenic C1'), 112.21 (15.39, C1), 116.03 (21.07, C3), 116.16 (22.18, C3'), 119.50 (3.41, C1'), 124.50 (3.67, C6), 130.57 (8.04, C4), 133.99 (8.15, C5 or C2'), 134.16 (8.5, C5 or C2'), 163.24 (252.45, C2 or C4'), 163.32 (250.7, C2 or C4'); IR (CDCl$_3$) 2263 (w), 2247 (etynyl stretch, w), 1600 (C=C), 1574 (w), 1510 (s), 1489, 1451, 1264, 1228, 1156, 1096, 1029 (w) cm$^{-1}$. MS (EI) m/e 214 (M+, 100).

Example 39

3,4'difluorodiphenylacetylene

A similar procedure to Example 30 but using [(4-fluorophenyl)methyl]-1H-benzotriazole (1.14 g, 5 mmol) and (3-fluorophenyl)methylenebenzenamine (1.00 g, 5 mmol), gave the title acetylene after recrystallization (60%) needle: mp 88°-89° C. (MeOH).

Example 40

Bis(2-naphthyl)acetylene

A procedure similar to Example 16 using N-([2-naphthalenyl]methylene)benzenamine and 2-naphthylmethyl chloride gave a 76% yield of product: mp 225°-226° C. (MeOH) (lit.[1] mp 228°-229° C.).

[1]Nakasuji, K.; Akiyama, S.; Akashi, K.; Nakagawa, M. *Bull. Chem. Soc. Jpn.* 1970, 43, 3567.

Example 41

Bis(1-naphthyl)acetylene

A procedure similar to Example 16 using N-([1-naphthalenyl]methylene)benzenamine and 1-naphthylmethyl chloride gave a 67% yield of product: mp 127°-128° C. (MeOH) (lit.[1] mp 129° C.).

[1]Nakasuji, K.; Akiyama, S.; Akashi, K.; Nakagawa, M. *Bull. Chem. Soc. Jpn.* 1970, 43, 3567.

Example 42

Methylenebis(4-oxyphenylethynyl)bisbenzene

A procedure similar to Example 16 but using [phenylmethyl]-1H-benzotriazole (2.09 g, 10 mmol) and 4,4'-methylenedioxybis(phenylmethylene)dianiline[1] (2.02 g, 5 mmol) for 1 h at 75° C. gave after chromatography (PE/EtOAc 4:1) the title acetylene (30%): mp 140°-143+ C. (cyclohexane); $^1$H NMR (200 MHz, CDCl$_3$) δ 5.74 (s, 2H, CH$_2$), 7.05-7.10 (m, 4H), 7.30-7.35 (m, 6H), 7.45-7.52 (m, 8H); $^{13}$C NMR (300 MHz, CDCl$_3$) δ 88.58 (acetylenic C), 88.97 (acetylenic C), 90.70, 116.36, 117.41, 123.36, 128.08, 128.31, 131.48, 133.09, 156.72; IR (CDCl$_3$) 3062 (w), 2978 (w), 2911 (w), 2217 (w, acetylenic stretch), 1599, 1573 (w), 1509, 1443 (w), 1414 (w), 1314 (w), 1279 (w), 1233, 1209 (s), 1175, 1137 (w), 1103 (w), 1014, 836 cm$^{-1}$. MS (EI) m/e 400 (M+, 64), 207 (100), 194 (18.7), 177 (83.7), 165 (24.3), 151 (27.0).

[1]Prepared as described previously: Paventi, M.; Hay, A. S. *Synthesis* 1990, 878.

Example 43

2-(2-Phenylethynyl)furan

A procedure similar to Example 16 but with 2-(N-phenylaminomethylidine)furan (0.86 g, 0.005 mol) and (phenylmethyl)-1H-benzotriazole (1.05 g, 0.005 mol) gave after workup and chromatography (PE/EtOAc 4:1) an oil (90%, 98.5% pure) (lit.[1] oil bp 74° C./0.1 mm Hg) which darkened on standing: $^1$H NMR (270 MHz, CDCl$_3$) δ 6.61 (dd, J=3 4 3.33, 2 3 1.98 Hz, 1H, C3H), 6.855 (d, 1H), C4H), 7.52-7.55 (m, 3H, phenyl), 7.616 (d, 1H, C2H), 7.71 (m, 2H, phenyl); $^{13}$C NMR (270 MHz, CDCl$_3$) δ 79.38 (C$\underline{C}$(C$_4$H$_4$O)), 93.22 (Ph$\underline{CC}$), 111.03 (C4), 115.19 (C3), 122.25 (C1'), 128.35 (C3'), 128.65 (C4'), 131.38 (C2'), 137.12 (C2), 143.59 (C5); MS (EI) m/e 168 (M+, 100), 139 (96.8).

[1]Teitei, T.; Collin, P. J.; Sasse, W. H. F. *Aust. J. Chem.* 1972, 25, 171.

Example 44

3-(2-Phenylethynyl)pyridine

A procedure similar to Example 16 but with 3-(N-phenylaminomethylidine)-pyridine (0.911 g, 0.005 mol) and (phenylmethyl)-1Hbenzotriazole (1.05 g, 0.005 mol) gave after workup and chromatography (PE/EtOAc 4:1) and treatment with boiling PE white needles (80%): mp 47°-48° C. (PE) (lit.[1] mp 47°-48.5° C., acetylenic stretch 2200 cm$^{-1}$); MS (EI) m/e 179 (M+, 100), 126 (21.7).

[1]Castro, C. E.; Gaughan, E. J.; Owsley, D. C. *J. Org. Chem.* 1966, 31, 4071.

V. Synthesis of Indoles

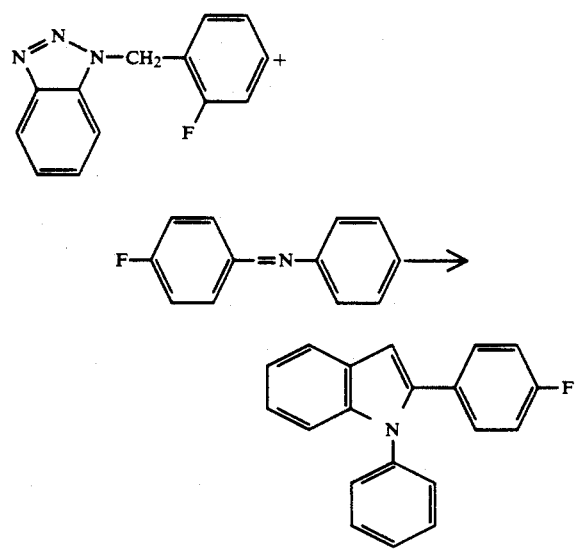

Example 45

1-Phenyl-2-(4-fluorophenyl)-1H-indole

A solution of (2-fluorophenyl)methyl-1H-benzotriazole (1.13 g, 5 mmol) and N-[(4-fluorophenyl)methylidine]benzenamine (0.996 g, 5 mmol) in DMF (7 mL) was stirred into potassium t-butoxide (1.68 g, 15 mmol) in DMF (18 mL) preheated to 75° C. The reaction monitore by HPLC showed completion upon mixing. After 11 minutes the DMF solution was poured in ice-cold $H_2O$ (75 mL) extracted with $CHCl_3$ (3×50 mL) and the solvent was evaporated. Chromatography first using PE as eluted 1-(4-fluorophenylethynyl)[2-fluorobenzene] (vide infra) then the eluant was changed to PE/EtOAc 97:3 eluting the title indole (40%): mp 126°–128° C. (MeOH); $^1$H NMR (200 MHz, $CDCl_3$) δ 6.77 (s, 1H, C3H), 6.94 (t, J=8.7 Hz, 2H, phenic H), 7.16–7.48 (m, 10H), 7.66–7.72 (m, 1H); MS (EI) m/e 287 (M+, 100).

VI. Polymer Synthesis

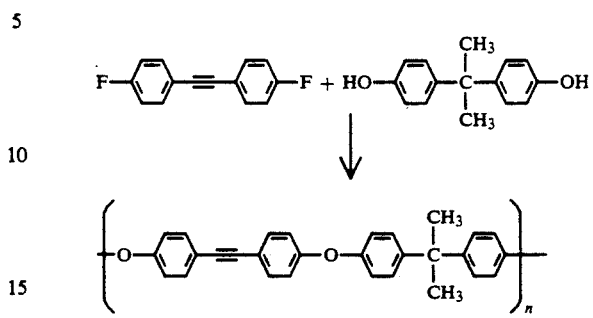

Example 46

Poly(phenylene ether yne

A mixture of 4,4'-(1-Methylethylidene)bisphenol (BPA) (1.141 g, 5 mmol), 4,4'-difluorodiphenylacetylene (1.071 g, 5 mmol) and anhydrous $K_2CO_3$ (0.9 g, mmol) in toluene (10 mL) and N-methylpyrrolidone (NMP) (14 mL) was stirred and heated to the reflux temperature of toluene azeotropically removing the water for 5 hours under a slow stream of $N_2$. The temperature was allowed to increase to 180° C. over a period of 5 hours allowing for the removal of toluene and NMP (4 mL). The dark mixture was then allowed to stir for an additional 10 hours when an aliquot flooded in MeOH precipitated high molecular weight polymer. The organics were cooled, filtered through celite, precipitated (MeOH), and dissolved in $CHCl_3$, filtered and reprecipitated (MeOH), washed ($H_2O$) and dried to yield 1.57 g of the title polymer: Tg=163° C. exotherm maximum 393° C. (temperature ramped at 20° C./min), ηinh 0.69 dL/g (TCE, 2.54° C.), Mw=54400 Mn=23300.

VII. Copolymer Synthesis

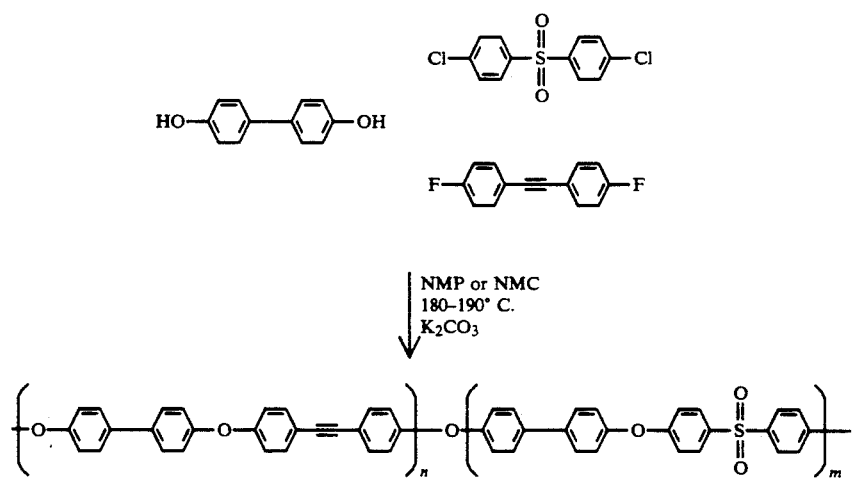

The following copolymers were synthesized as in Example 43 using the molar amounts of 4,4'difluorodiphenylacetylene and 4,4'dichlorodiphenyl sulfone shown in Table 2.

TABLE 2

| | | | | | TGA (°C.) | | | |
|---|---|---|---|---|---|---|---|---|
| | n | m | Inherent | Tg | Tg after curing | | | |
| Example | (mol %) | (mol %) | Viscosity | (°C.) | 1 hr @ 340° C. | N₂ (−10%) | Air | Film | Solubility |
| 47 | 5 | 95 | 0.39 | 208 | 218 | 511 | 522 | Brittle | CH₂Cl₂/CHCl₃ |
| 48 | 10 | 90 | 0.4 | 210 | 225 | 526 | 530 | Brittle | CH₂Cl₂/CHCl₃ |
| 49 | 30 | 70 | 0.64 | 188 | 277 | 522 | 531 | Brittle | NMP/TCE (hot) |

We claim:

1. An enamine of formula (II):

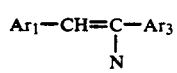

(II)

wherein Ar₁ and Ar₃ are each independently selected from aryl of 6 to 16 carbon atoms and hetaryl selected from the group consisting of pyridinyl, furanyl, thiophenyl, thiazolyl and quinolinyl, unsubstituted or substituted, one or more times, by radicals selected from F, Cl, Br; alkyl of 1 to 6 carbon atoms; alkenyl of 2 to 6 carbon atoms; aryl of 6 to 12 carbon atoms; aralkyl of 7 to 18 carbon atoms; aralkenyl of 8 to 18 carbon atoms, alkoxy of 1 to 6 carbon atoms; thioalkoxy of 1 to 6 carbon atoms; aryloxy of 6 to 12 carbon atoms; and thioaryloxy of 6 to 12 carbon atoms; and —N is a hetaryl radical selected from the group consisting of benzimidazolyl and benzotriazolyl, provided that when said hetaryl radical —N is benzotriazolyl, Ar₁ and Ar₃ are each independent selected from said unsubstituted or substituted hetaryl.

2. An enamine according to claim 1 wherein said hetaryl radical —N is benzimidazolyl.

3. An enamine according to claim 1 wherein said hetaryl radical —N is benzotriazolyl.

4. An enamine according to claim 2 wherein Ar₁ and Ar₃ are each independently selected from said unsubstituted or substituted hetaryl.

5. An enamine according to claim 2 wherein Ar₁ and Ar₃ are aryl radicals independently selected from

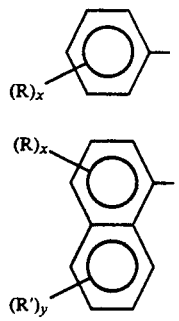

-continued

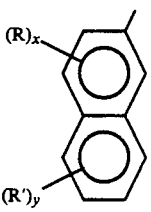

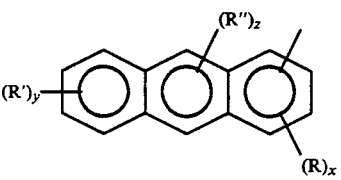

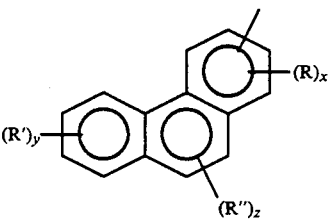

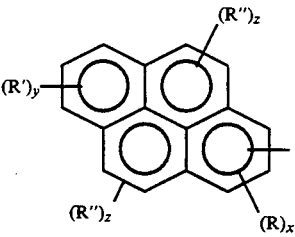

wherein x and y are integers independently selected from 0, 1, 2 or 3, z is an integer independently selected from 0, 1 or 2 and R, R' and R" are each independently selected from halogen atoms selected from fluorine, chlorine and bromine; alkyl of 1 to 6 carbon atoms, alkenyl of 2 to 6 carbon atoms; aryl of 6 to 12 carbon atoms, aralkyl of 7 to 18 carbon atoms; aralkenyl of 8 to 18 carbon atoms; alkoxy of 1 to 6 carbon atoms; thioalkoxy of 1 to 6 carbon atoms; aryloxy of 6 to 12 carbon atoms and thioaryloxy of 6 to 12 carbon atoms.

* * * * *